United States Patent [19]
Marshall et al.

[11] Patent Number: 5,643,214
[45] Date of Patent: Jul. 1, 1997

[54] INJECTION DEVICES

[75] Inventors: Jeremy Marshall; Derek Turner, both of Oxford, United Kingdom

[73] Assignee: Owen Mumford Limited, Oxford, United Kingdom

[21] Appl. No.: 373,322

[22] PCT Filed: May 13, 1994

[86] PCT No.: PCT/GB94/01036

§ 371 Date: Jan. 18, 1995

§ 102(e) Date: Jan. 18, 1995

[87] PCT Pub. No.: WO94/26331

PCT Pub. Date: Nov. 24, 1994

[30] Foreign Application Priority Data

May 18, 1993 [GB] United Kingdom ............ 9310163

[51] Int. Cl.⁶ .................. A61M 5/20; A61M 5/315
[52] U.S. Cl. ............... 604/134; 604/135; 604/131
[58] Field of Search ........................... 604/156, 157, 604/134, 135, 136

[56] References Cited

U.S. PATENT DOCUMENTS 4,394,863  7/1983  Bartner ........................... 604/157
5,114,406  5/1992  Gabriel ........................... 604/136
5,300,030  4/1994  Crossman ....................... 604/156

Primary Examiner—Sam Rimell
Assistant Examiner—Luke J. Yeh
Attorney, Agent, or Firm—Young & Thompson

[57] ABSTRACT

An injection device is adapted to eject a sequence of doses from the needle of a capsule carried within its barrel-like body. A plunger extending rearwardly from the capsule has ratchet teeth along its length engaged by pawls at the forward end of a drive tube biased forwardly by a spring. The capsule is in a sleeve-like carrier having limited longitudinal travel, a lost motion connection to the drive tube and an engagement with the ratchet teeth by pawls. The drive tube can be releasibly retained in a rearward position by a trigger mechanism. When released, the drive tube urges the plunger, capsule and carrier forwards to project the needle. The liquid acts effectively as a solid. With the carrier stopped, the plunger carries on to eject a dose, clicking past the carrier pawls. The re-prime, the knob is pulled to retract the drive tube and the carrier, the lost motion connection allowing the drive tube to move further and have its pawls click back along the plunger until the trigger mechanism re-engages.

9 Claims, 5 Drawing Sheets

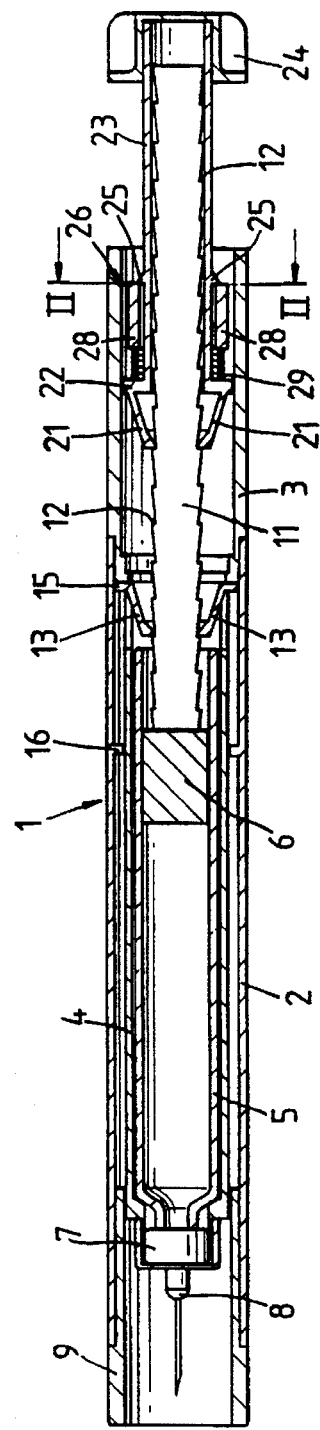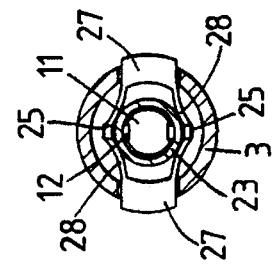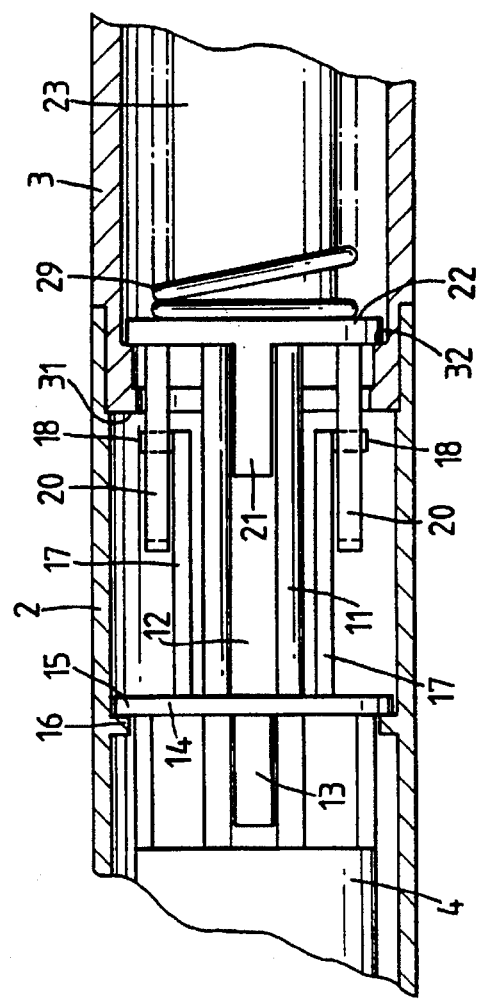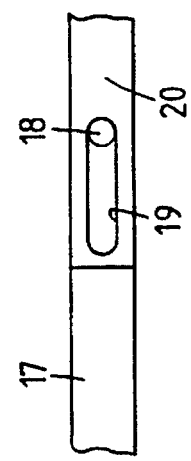
Fig. 1
Fig. 2
Fig. 3
Fig. 4

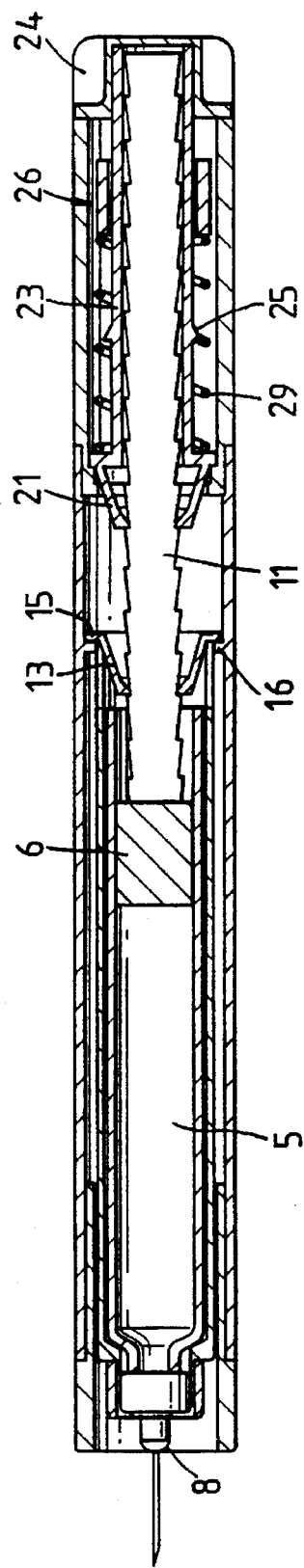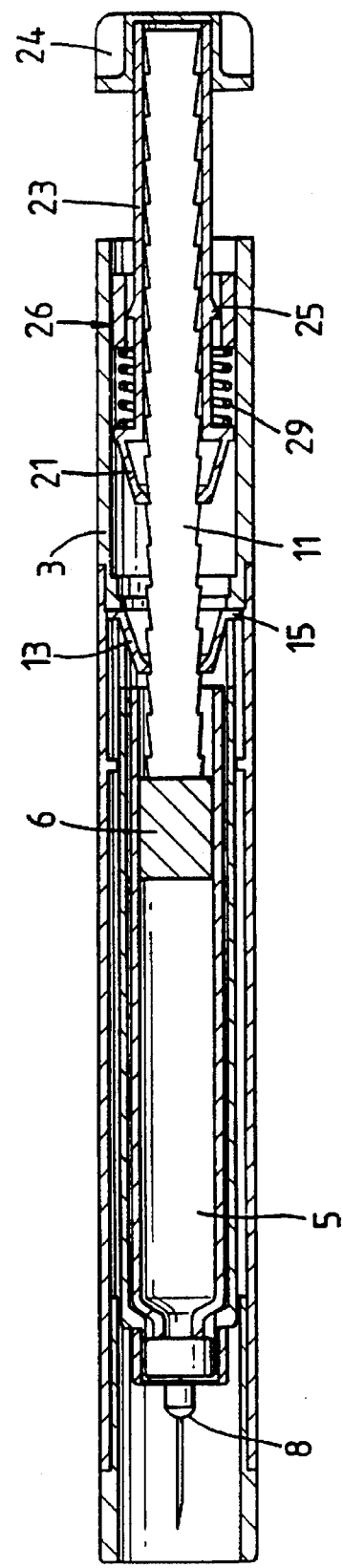
Fig. 5A
Fig. 5B

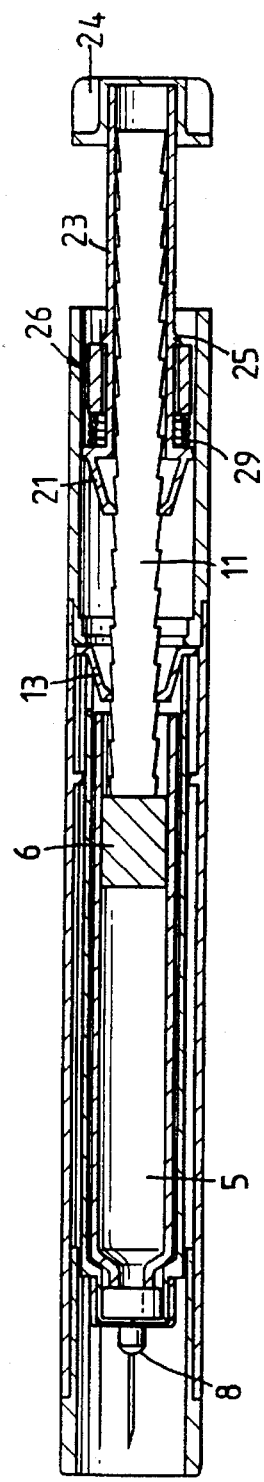
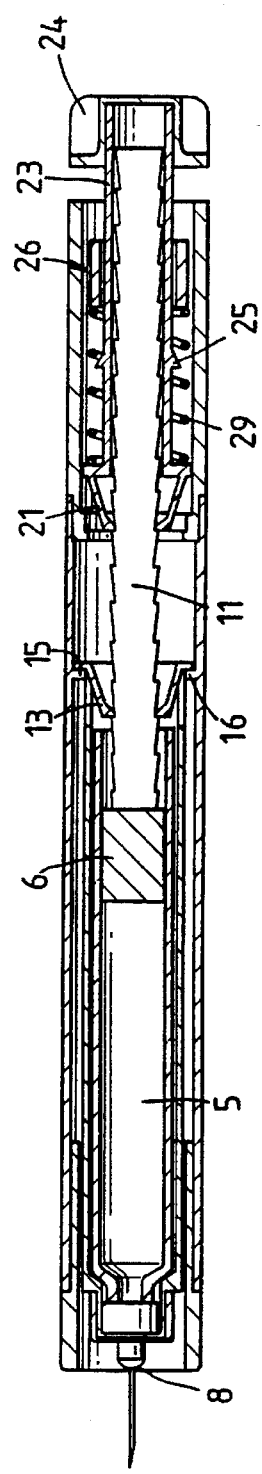
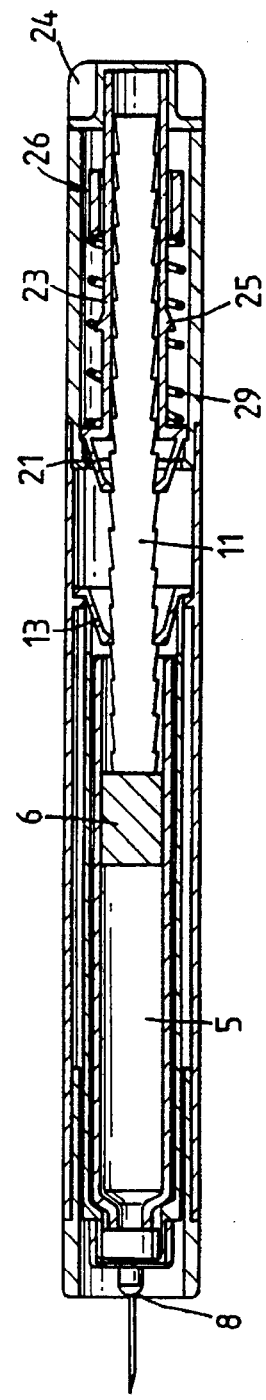

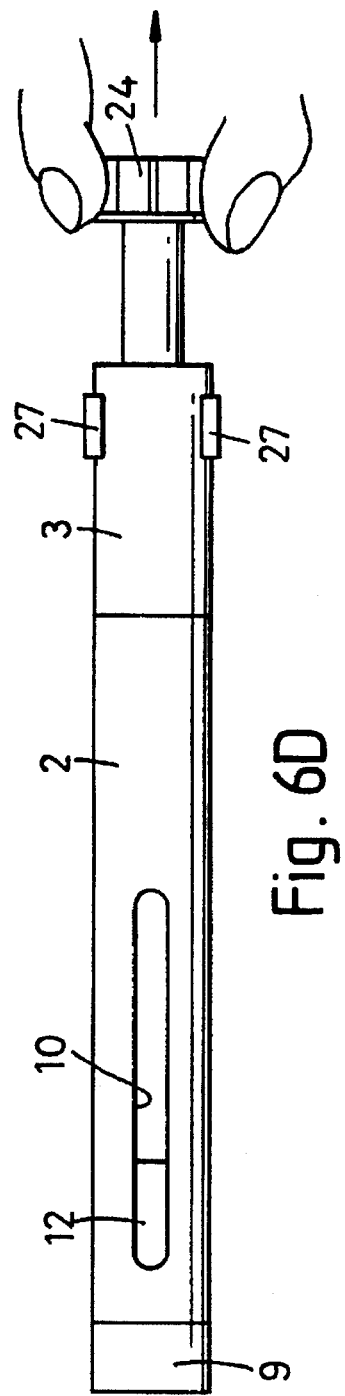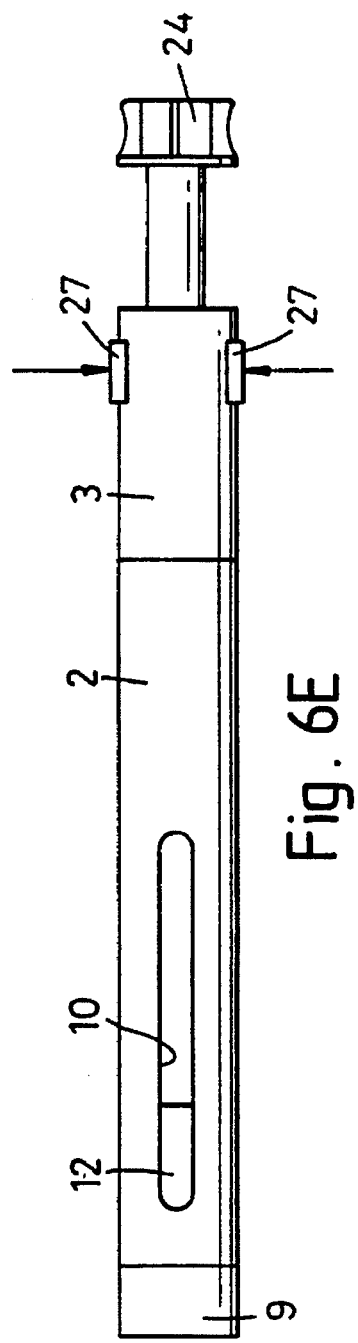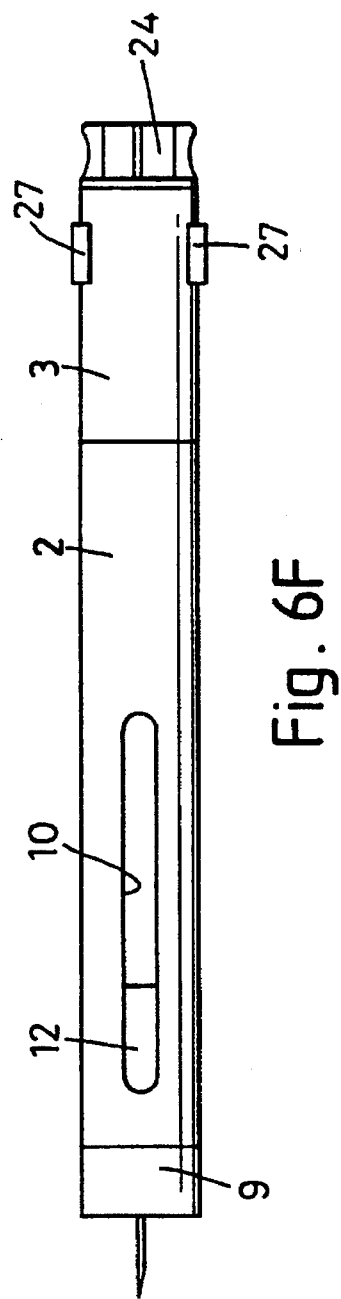

INJECTION DEVICES

This invention relates to injection devices.

Often, when a sequence of injections is carried out, each time the entire contents of a capsule are ejected through the needle in a single stroke of a plunger. However, there are other circumstances where only a small amount of fluid should be used, and it is not always practical or economic to make a number of very small capsules and injection devices to cater for this. There is therefore a need for an injection device which can produce repeated measured doses from a single capsule. It is the aim of this invention to provide one.

According to the present invention there is provided an injection device with an elongate barrel-like body for giving a sequence of injections of liquid from a capsule, the capsule being carried therein in a manner allowing longitudinal movement between limiting positions, having a needle at one, forward end and a plunger extending rearwardly from the other end whose operation causes emission of doses through the needle, the device comprising spring drive means with a limited travel which, when energised, engages the plunger at a first position thereon and urges it forwardly, the drive in a first phase carrying the capsule from a rear to a forward limit, by virtue of a substantial hydraulic lock, to project the needle from the body, and in a second phase forcing the plunger alone on to eject a dose, manually operable priming means to re-energise the drive means and withdraw the capsule to its rear limit, the plunger being carried with the capsule until the spring drive means re-engages the plunger at a second position more rearward thereon than the first position, and means for releasably holding the spring drive means energised after priming.

Thus, on the forward stroke, the plunger first pushes the capsule forwards to its limit by acting on the liquid in the capsule which is effectively solid, and then carries on more slowly to eject one dose. The plunger is then stopped, but at a position further forward with respect to the capsule than before that operation. For the next dose, the priming means pulls back the plunger and capsule and re-energises the spring drive means, which is temporarily held by a trigger mechanism. But before it achieves this, the capsule carrier will reach its rearward limit, while the drive means has its relationship to the plunger adjusted to compensate for the emission of one dose. The device is then ready for the next injection.

Preferably, the plunger and drive means have pawl and ratchet interengagement, positive in the drive direction, the ratchet teeth generally being on the plunger while the pawl is on the drive means.

The capsule may be mounted in a carrier capable of longitudinal movement within the body, limited by stops. It too preferably has a pawl to engage the ratchet teeth, and it will then also have a lost motion connection with the drive means. During the first phase of the drive stroke the carrier is driven directly via the plunger, the liquid and the capsule and the lost motion connection contributes nothing. But during the second phase of the drive stroke, with the carrier arrested, the carrier pawl has its engagement with the teeth shifted to the rear as the lost motion connection allows relative movement between the drive means and the carrier. After injection and when the device is primed again, the lost motion connection ensures that both carrier and drive means are withdrawn by different amounts, allowing the pawl of the drive means to have its engagement with the teeth shifted to the rear. These shifts, and the scope of the lost motion, correspond to the movement of the plunger relative to the capsule when ejecting a single dose.

Conveniently, the drive means includes a tubular member sleeved over the plunger with coil spring means encircling it and effectively reacting against the body. The priming means may simply be a knob on the end of the tubular member accessible at the rear end of the body.

The means for releasably holding the drive means may be a trigger device carried by the body and arranged to engage a detent on the tubular member when that member is withdrawn rearwardly from the body to a predetermined extent. Preferably, it comprises diametrically opposed pads accessible outside the body and connected by springy webs within the body which encircle the tubular member to engage diametrically opposed detents on that member when withdrawn. Squeezing of the pads together causes the webs to diverge and release from the detents. Conveniently, the or each detent has a snap action engagement with the trigger when the tubular member reaches its predetermined withdrawn position.

For a better understanding of the invention, one embodiment will now be described, by way of example, with reference to the accompanying drawings, in which:

FIG. 1 is an axial section of an injection device,

FIG. 2 is a cross section on the line II-II of FIG. 1,

FIG. 3 is an axial section, to an enlarged scale, of part of the device of FIG. 1, the sectional plane being at right angles to that of FIG. 1, FIG. 4 is a detail of a lost motion coupling also shown in FIG. 3, FIG. 5 shows further axial sections of the device in various stages of operation.

Figure 6A:
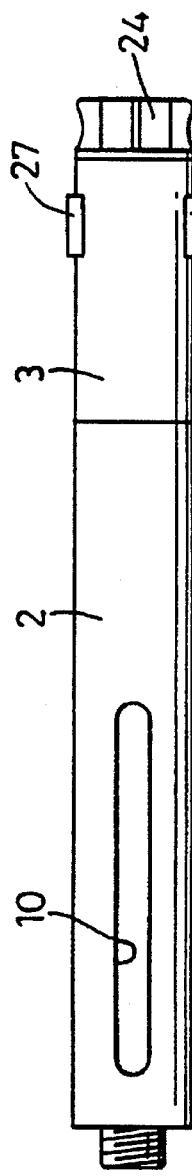
FIG. 6 shows side views of the device in various stages of operation.

The device has a cylindrical barrel 1 comprising two tubes 2 and 3 with a telescoped joint. Within the forward, longer cylindrical tube 2 there is a co-axial sleeve 4 inside which is carried a capsule 5 containing the liquid to be injected. It has a piston 6 initially near its rear end when the capsule is full, and its forward end has a neck fitted with a cap 7 which seals the capsule by a membrane and which locates within a reduced forward end portion of the sleeve 4. A needle assembly 8 can be screwed over this reduced forward end and, when fully fitted, the rear end of the needle penetrates the membrane to open a very fine passage for the liquid in the capsule through the needle.

Figure 6B:
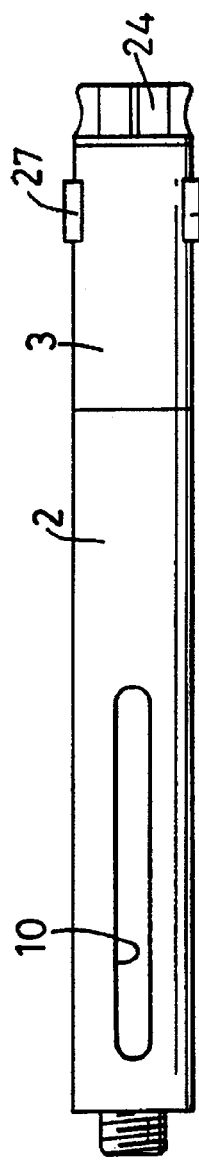
Figure 6C:
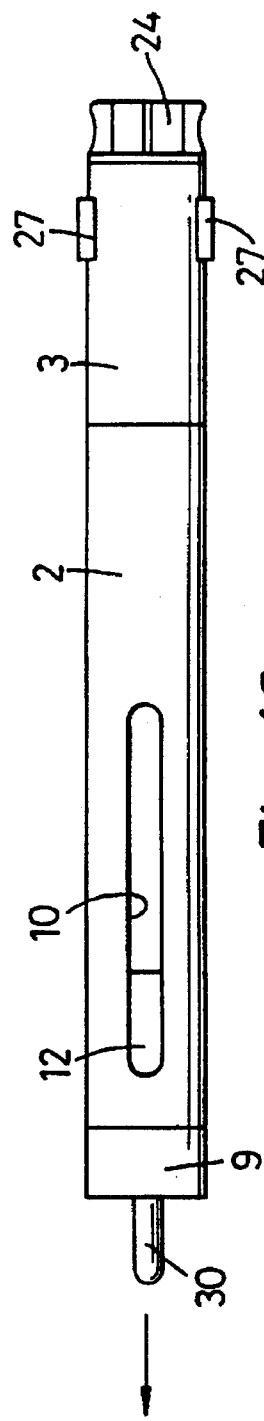

The needle assembly 8 is largely shrouded by a cylindrical insert 9 which plugs into the forward end of the tube 2. When the needle is retracted, as shown in FIG. 1, the tip is within this insert 9, but when the device is fired as will be described later, the needle will project proud of the insert 9. The extent of this projection, and hence the depth to which the needle will penetrate, may be determined by the setting of the insert 9. As shown in FIG. 1, it plugs fully into the tube 2, giving a maximum projection of the needle when used. But it could be removed, rotated and plugged in again, and with appropriate formations, such as co-operating grooves and ribs, it may then be set to extend the barrel 1 slightly, and thus reduce the amount of needle penetration. As seen in FIG. 6, the tube 2 has an elongate window 10 in which part of the insert 9 will appear, and this may have a marking to indicate, in millimeters for example, the amount of penetration given by that setting.

The piston 6 abuts a rearwardly extending rod 11 which is formed with ratchet teeth 12, their pitch corresponding to the dosage delivered by one actuation of the device. The steep, abutment faces of the ratchet teeth face rearwardly and are engaged by two sets of pawls. One set of pawls 13 incline forwardly and inwardly from a cage-like formation at the rear end of the sleeve 4. This terminates in a disc 14 centrally apertured for free passage of the rod 11 and of larger diameter than the main body of the sleeve 4 so that it provides an outer annular rib 15 whose forward face initially abuts against an internal rib 16 of the tube 2. These ribs 15 and 16 and the interior of the insert 9 maintain the sleeve 4 co-axial with the barrel 1.

Extending further rearwardly from the disc 14 there are two parallel diametrically opposed fingers 17 with outwardly projecting studs 18 at their free ends. These engage in slots 19 in associated parallel legs 20 which alternate circumferentially with the pawls 21 of the other set engaging the teeth 12. The legs 20 and pawls 21 extend forwardly from an annular flange 22 at the forward end of a tube 23 which sleeves over the rod 11 and which has a priming knob 24 at its rear end, beyond the barrel 1. At an intermediate point of the tube 23 there are diametrically opposed external abutments 25 in the form of saw teeth with the sloping sides facing rearwardly and the steep sides facing forwardly.

Near the rear end of the tube 3 there is a release mechanism 26. This comprises two diametrically opposed pads 27 located within apertures in the tube 3 and connected by resilient, flexible webs 28 which spread to embrace the tube 23. These pads 27 are normally proud of the exterior of the tube 3. Between the rear face of the flange 22 and this release mechanism 26 there is a coil spring 29 surrounding the tube 23.

For use, it will be assumed that the insert 9 will be fitted at the appropriate setting and that a needle cover 30, which is usually provided as shown in FIG. 6, has been removed. The device is then in the condition as shown at A in FIG. 5 and C in FIG. 6 with the ribs 15 and 16 abutting, the spring 29 extended and relaxed, and the studs 18 at the rear ends of the slots 19.

The user primes the device by grasping the barrel 1 in one hand and pulling the knob 24 by the other. The sleeve 4 has very little resistance to rearward movement from its initial position and, by virtue of the pawls 21 at least, the tube 23 does exert some grip on the rod. Therefore, pulling the knob 24 also draws back the rod 11 and that, acting through the pawls 13, carries the sleeve 4 and the capsule 5 with it. Thus the tip of the needle is withdrawn within the insert 9. This position is shown at B in FIG. 5 and D in FIG. 6.

The rearward movement of the sleeve 4, the capsule 5 and the rod 11 is limited by the rib 15 coming up against the forward end 31 of the tube 3. However, the tube 23 can continue by virtue of the lost motion mechanism provided by the studs 18 and the slots 19, and as it does so the abutments 25 which have wedged between the webs 28 pass to the rear of the release mechanism 26 as shown at C in FIG. 5, and in FIG. 1. This extra movement of the tube 23 means that the pawls 21 click over one pair of teeth 12 on the rod 11.

In the event of any resistance to the free rearward movement of the sleeve 4, the tube 23 will at first move independently. But the lost motion connection will ensure that, after it has travelled the pitch of one pair of teeth 2, the sleeve 4 will follow, and will reach its rearward limit as the abutments 25 snap past the webs 28. Thus the relative displacement between the pawls 13 and the pawls 21 is limited to a distance equal to the pitch of one pair of teeth 12.

In any event, whatever the sequence of movement of the sleeve 4 and the tube 23, the device is now primed.

For the actual injection, the insert 9 is held against the user's skin, and the pads 27 are squeezed. This spreads the webs 28 sufficiently for them radially to clear the abutments 25. The spring 29 can now exert itself and push the tube 23 forwards. By the engagement of the pawls 21 with the rod 11, the latter is also pushed forwards. Since, by virtue of the liquid in the capsule 5 and the very fine bore of the needle, the piston 6 is virtually solid with the capsule, the first effect is for the piston to carry the sleeve 4 and capsule 5 forwards, projecting the needle. But this movement is arrested when the ribs 15 and 16 re-engage. This is shown at D in FIG. 5. But there is still scope for further movement of the tube 23, and the spring 29 now pushes the piston 6 alone, via the pawls 21 and the rod 11, until the rear ends of the slots 19 come up against the now stationary studs 18 and/or the flange 22 abuts against an internal shoulder 32 of the tube 3. This movement forces out a measured dose from the capsule 5. During this second phase the pawls 13 click over one pair of teeth and so the device is then in its original condition, except that the pawls 13 and 21 each engage the pairs of teeth 12 one further back from the pairs previously engaged.

Further injections can be carried out by the same process and it will be seen that the same dose will be administered each time, corresponding to the pitch of the teeth 12.

The ratchet teeth 12 may be annular so that it will not matter how the capsule 5 is rotationally positioned. Alternatively, and as illustrated in FIGS. 2 and 3, they may form sunken racks along diametrically opposite sides of the rod 11. The pawls will thus be confined by the shoulders along the sides of the racks and prevent the parts that move longitudinally of the barrel i mutually rotating. However, with separate, diametrically opposed abutments 25, provision may be made to stop this assembly as a whole rotating. If the tube 23 was twisted by the knob 24 from the FIG. 2 position, it could release the abutments 25 from the webs 28. The flange 22 could have one or more lugs engaged in longitudinal grooves on the inside of the tube 3, for example. Alternatively, the abutments 25 could be combined into an annular, tooth-sectioned rib so that twisting the knob 24 would have no effect.

We claim:

1. An injection device with an elongate barrel-ilke body for giving a sequence of injections of liquid from a capsule, the capsule being carried therein in a manner allowing longitudinal movement between limiting positions, and having a needle at one, forward end and a piston actuable through the other, rear end to cause emission of doses through the needle, the device comprising a plunger to act on the piston, spring drive means with a limited travel and with a pawl and ratchet engagement with the plunger to drive the plunger in the forward direction, manually operable priming means to energise the drive means to withdraw the capsule to its rear limit, and means for releasably holding the spring drive means energised after priming, wherein the energised spring means engages the plunger at a first position thereon and when released drives the plunger and thus the piston forwardly, the drive in a first phase carrying the capsule from a rear to a forward limit by virtue of the contents of the capsule, with escape only through the needle, forming a substantial hydraulic lock, the needle then projecting from the body, and in a second phase forcing the piston alone on to eject a dose, and wherein the priming means when operated carries the plunger rearwardly with the capsule until the spring drive means re-engages the plunger at a second position more rearward thereon than the first position.

2. An injection device as claimed in claim 1, characterised in that the ratchet teeth (12) are on the plunger (11) and the pawl (21) is on the drive means (23,29).

3. An injection device as claimed in claim 1, characterised in that the capsule (5) is mounted in a carrier (4) capable of longitudinal movement within the body, limited by stops (16,31).

4. An injection device as claimed in claim 2, characterised in that the carrier (4) has a pawl (13) to engage the ratchet teeth (12) and a lost motion connection (18,19) with the drive means (23,29) whereby, on the second phase of the drive stroke, the carrier pawl (13) has its engagement with the teeth (12) shifted to the rear as the lost motion connection (18,19) allows relative movement between the drive means (23,29) and the carrier (4), and whereby, on priming, the lost motion connection (18,19) ensures that both carrier (4) and drive means (23,29) are withdrawn but allows the pawl (21) of the drive means (23,29) to have its engagement with the teeth (12) shifted to the rear.

5. An injection device as claimed in claim 1, characterised in that the drive means (23,29) includes a tubular member (23) sleeved over the plunger (11) with coil spring means (29) encircling it and reacting against the body (1).

6. An injection device as claimed in claim 5, characterised in that the priming means is a knob (24) on the end of the tubular member (23) accessible at the rear end of the body (1).

7. An injection device as claimed in claim 5, characterised in that the means (25,28) for releasably holding the drive means (23,29) is a trigger device (26) carried by the body (1) and arranged to engage a detent (25) on the tubular member (23) when that member is withdrawn rearwardly from the body to a predetermined extent.

8. An injection device as claimed in claim 7, characterised in that the trigger device (26) comprises diametrically opposed pads (27) accessible outside the body (1) and connected by springy webs (28) within the body which encircle the tubular member (23) to engage diametrically opposed detents (25) on that member when withdrawn, squeezing of the pads (27) together causing the webs (28) to diverge and release from the detents (25).

9. An injection device as claimed in claim 7, characterised in that the detent (25) has a snap action engagement with the trigger device (26) when the tubular member (23) reaches its predetermined withdrawn position.

* * * * *